United States Patent [19]

Bouzard et al.

[11] 4,012,382
[45] Mar. 15, 1977

[54] α-AMINO AND α-FORMYL-α-(p-ACYLOXYPHENYL) ACETAMIDOCEPHALOSPORANIC ACID DERIVATIVES

[76] Inventors: Daniel Bouzard, 2, Rue de Centre, 95130 Franconville, France; Abraham Weber, 55, Blvd. Soult, 75012 Paris, France

[22] Filed: May 27, 1975

[21] Appl. No.: 581,054

[30] Foreign Application Priority Data

June 5, 1974 United Kingdom ............ 24848/74

[52] U.S. Cl. .................. 260/243 C; 260/281 R; 260/302 D; 260/308 B; 260/471 R; 260/475 PN; 424/246
[51] Int. Cl.² ........................................ C07D 501/36
[58] Field of Search ................................ 260/243 C

[56] References Cited
UNITED STATES PATENTS

| 3,453,263 | 7/1969 | Duonch et al. | 260/243 C |
| 3,579,514 | 5/1971 | McGregor | 260/243 C |
| 3,668,203 | 6/1972 | Clark et al. | 260/243 C |
| 3,701,775 | 10/1972 | Berges et al. | 260/243 C |
| 3,753,977 | 8/1973 | Fechtig et al. | 260/239.1 |
| 3,813,388 | 5/1974 | Crast | 260/239.1 |
| 3,855,213 | 12/1974 | Dunn et al. | 260/243 C |
| 3,867,380 | 2/1975 | Dunn et al. | 260/243 C |
| 3,868,369 | 2/1975 | Berges | 260/243 C |
| 3,931,160 | 1/1976 | Dunn | 260/243 C |
| 3,943,129 | 3/1976 | Berges | 260/243 C |
| 3,953,439 | 4/1976 | Gleason | 260/243 C |

FOREIGN PATENTS OR APPLICATIONS

| 1,277,415 | 6/1972 | United Kingdom | 260/243 C |
| 1,319,173 | 6/1973 | United Kingdom | 260/243 C |
| 1,326,531 | 8/1973 | United Kingdom | 260/243 C |
| 1,334,382 | 10/1973 | United Kingdom | 260/243 C |
| 1,342,241 | 1/1974 | United Kingdom | 260/243 C |
| 1,082,943 | 9/1967 | United Kingdom | 260/243 C |
| 1,082,962 | 9/1967 | United Kingdom | 260/243 C |
| 1,241,656 | 8/1971 | United Kingdom | 260/243 C |

Primary Examiner—Nicholas S. Rizzo
Assistant Examiner—David E. Wheeler
Attorney, Agent, or Firm—Herbert W. Taylor, Jr.

[57] ABSTRACT

This invention relates to certain novel α-amino- or α-formyl-α-(p-acyloxyphenyl)acetamidocephalosporanic acids which are useful as antibacterial agents.

1 Claim, No Drawings

α-AMINO AND α-FORMYL-α-(p-ACYLOXYPHENYL)- ACETAMIDOCEPHALOSPORANIC ACID DERIVATIVES

FIELD OF THE INVENTION

The chemical compounds of the present invention are antibacterial agents of the class commonly called cephalosporins.

SUMMARY OF THE INVENTION

The novel cephalosporin derivatives of this invention comprise the D-(—) compounds of the formula

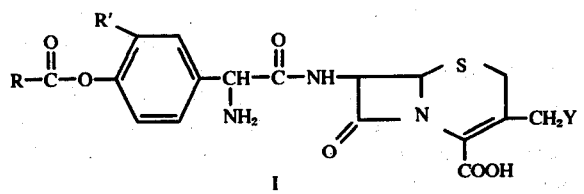

wherein Y is hydrogen or S-Het, in which Het represents a 5 or 6 membered heterocyclic ring containing 1 to 4 atoms selected from N, O or S, said heterocyclic ring being optionally substituted by $C_1$–$C_4$ alkyl which may be optionally substituted by a carboxylic acid group or hydroxy, or alkoxyalkyl of up to 4 carbon atoms; R is hydrogen, $C_1$–$C_{10}$ alkyl optionally substituted by carboxylic acid, or phenyl optionally substituted by $C_1$–$C_4$ alkyl, halogen, nitro, amino or trifluoromethyl; R' is hydrogen, hydroxy, $C_1$–$C_4$ alkyl, $C_1$–$C_4$ alkoxy or halogen, and pharmaceutically acceptable salts thereof, when substantially free of the L-(+) isomer, and the D-(—) compounds of the formula I(a)

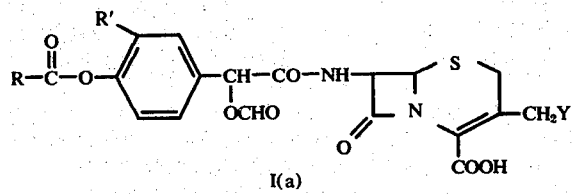

wherein Y is S-Het, in which Het is 1,2,3-triazol-5-yl, 1-N-methyl-tetrazol-5-yl or 2-methyl-1,3,4-thiadiazol-5-yl; R is hydrogen, $C_1$–$C_{10}$ alkyl optionally substituted by carboxylic acid, or phenyl optionally substituted by $C_1$–$C_4$ alkyl, halogen, nitro, amino or trifluoromethyl; R' is hydrogen, hydroxy, $C_1$–$C_4$ alkyl, $C_1$–$C_4$ alkoxy or halogen, and pharmaceutically acceptable salts thereof, when substantially free of the L-(+) isomer.

In the above compounds, the substituent halogen is preferably selected from fluorine, chlorine or bromine.

The pharmaceutically acceptable salts referred to above include the nontoxic carboxylic acid salts, e.g. nontoxic metallic salts such as sodium, potassium, calcium and aluminium, the ammonium salt and salts with nontoxic amines, e.g. trialkylamines, procaine, dibenzylamine, N-benzyl-β-phenethylamine, 1-ephenamine, N,N'-dibenzylethylenediamine, N-alkylpiperidine and other amines which are used to form salts of penicillins and cephalosporins. Also included within the definition of pharmaceutically acceptable salts are the nontoxic acid addition salts (amine salts), e.g. salts with mineral acids such as hydrochloric, hydrobromic, hydroiodic, phosphoric, sulfuric and salts with organic acids such as maleic, acetic, citric, oxalic, succinic, benzoic, tartaric, fumaric, mandelic, ascorbic and malic.

Examples of suitable heterocyclic groups included within the definition of "Het" in formula I are such heterocyclic radicals as thienyl, pyrazolyl, imidazolyl, isoimidazolyl, triazolyl, tetrazolyl, thiazolyl, thiadiazolyl, thiatriazolyl oxazolyl, oxadiazolyl, isothiazolyl, isoxazolyl, pyridyl, pyridazinyl, pyrazinyl, pyrimidinyl and triazinyl. The heterocyclic ring may be unsubstituted with one or more of the substituents as mentioned above.

Preferred D-(—) compounds of formula I are those wherein Y is hydrogen or S-Het, in which Het represents 1,2,3-triazolyl, 2-methyl-1,3,4-thiadiazol-5-yl, 2-methyl-1,3,4-oxadiazol-5-yl, 1-N-methyl-tetrazol-5-yl and 1,2,3,4-tetrazolyl; R is hydrogen, $C_1$–$C_4$ alkyl or phenyl optionally substituted by $C_1$–$C_4$ alkyl, fluorine, chlorine, nitro, amino or trifluoromethyl; and R' is hydrogen, or the above D-(—) compounds of formula I(a) wherein Y is S-Het, in which Het is 1,2,3-triazolyl, 2-methyl-1,3,4-thiadiazol-5-yl, or 1-N-methyl-tetrazol-5-yl; R is hydrogen or $C_1$–$C_4$ alkyl; and R' is hydrogen.

More preferred D-(—) compounds of formula I and I(a) are those in which Y is hydrogen or S-Het, in which Het is 1,2,3-triazolyl, 1-N-methyl-tetrazol-5-yl or 2-methyl-1,3,4-thiadiazol-5-yl; R is hydrogen or methyl; and R' is hydrogen.

The present invention also includes a process for the preparation of a compound of the formula

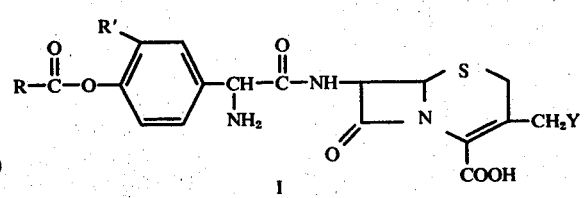

wherein Y is hydrogen or S-Het, in which Het represents a 5 or 6 membered heterocyclic ring containing 1 to 4 atoms selected from N, O or S, said heterocyclic ring being optionally substituted by $C_1$–$C_4$ alkyl which may be further optionally substituted by carboxylic acid, or alkoxyalkyl of up to 4 carbon atoms; R is hydrogen $C_1$–$C_{10}$ alkyl optionally substituted by carboxylic acid, or phenyl optionally substituted by $C_1$–$C_4$ alkyl, halogen, nitro, amino or trifluoromethyl; R' is hydrogen, hydroxy, $C_1$–$C_4$ alkyl, $C_1$–$C_4$ alkoxy or halogen, and pharmaceutically acceptable salts thereof when substantially free of the L-(+) isomer, which process comprises reacting a compound of the formula

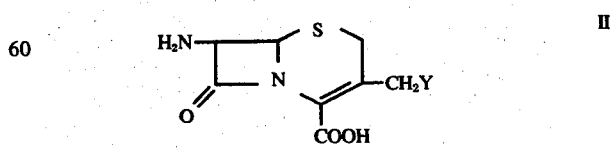

or a silyl ester or salt thereof in which Y is as defined above or acetoxy with a corresponding D-(—) acylating agent of an acid of the formula

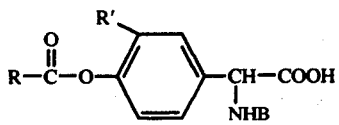

in which R and R' are as defined above and B is an amino-protecting group, and removing the amino-protecting group to produce the compound of formula I or a pharmaceutically acceptable salt thereof, and converting by methods known per se the compound of formula I, wherein Y is acetoxy, to the corresponding product wherein Y is S-Het and, if desired, either before or after removal of B, converting by methods known per se the product in the form of the free acid or silyl ester or salt thereof to the corresponding free acid or pharmaceutically acceptable salt thereof.

In the preparation of the novel cephalosporin compounds of the present invention, a corresponding 7-amino-cephalosporanic acid compound of formula II or salt thereof is acylated by known methods with the appropriate D-(−) acylating agent of formula III.

In the case of 3-thiolated-7-aminocephalosporanic acid intermediate of formula II, when Y is S-Het, said intermediate may be prepared by displacement of the 3-acetoxy group of 7-aminocephalosporanic acid or a salt thereof with the appropriate heterocyclic thiol or a slat thereof. The displacement of an ester group with a thiol group is a known reaction and is preferably accomplished in aqueous solution with heating.

The intermediate II may, if desired, by converted prior to the acylation reaction to a silyl ester or acid addition salt thereof. The silyl esters may be prepared by the methods described in the literature, e.g. U.S. Pat. No. 3,249,622. The silyl ester group may be removed following the acylation reaction by hydrolysis.

Prior to the acylation reaction the amino group of the acylating agent III may be protected by a conventional amino-blocking group B respectively, which may be readily removed at the conclusion of the reaction by methods known per se. Examples of suitable amino-protecting or blocking groups include t-butoxycarbonyl, carbobenzyloxy, 2-hydroxy-1-naphthcarbonyl, trichloroethoxycarbonyl, 2-ethoxycarbonyl-1-methylvinyl and 2-methoxycarbonyl-1-methylvinyl. A particularly valuable blocking group is a proton, as in the compound of the formula

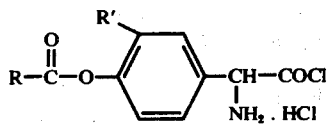

For example, following the acylation coupling reaction, it can be easily removed by neutralization. Obviously other functionally equivalent blocking groups for an amino group can be used and such groups are considered within the scope of this invention.

In addition to the above, the present invention also includes a process for the preparation of a compound of the formula I(a) wherein Y is S-Het, in which Het is 1,2,3-triazol-5-yl, 1-N-methyl-tetrazol-5-yl or 2-methyl-1,3,4-thiadiazol-5-yl; R is hydrogen, $C_1$–$C_{10}$ alkyl optionally substituted by carboxylic acid, or phenyl optionally substituted by $C_1$–$C_4$ alkyl, halogen, nitro, amino or trifluoromethyl; R' is hydrogen, hydroxy, $C_1$–$C_4$ alkyl, $C_1$–$C_4$ alkoxy or halogen, and pharmaceutically acceptable salts thereof, when substantially free of the L-(+) isomer, which process comprises reacting a compound of the formula II, in which Y is as immediately defined above or a silyl ester or salt thereof with a corresponding D-(−) acylating agent of an acid of the formula

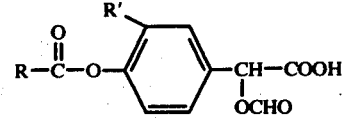

in which R and R' are as defined immediately above, to produce the compound of formula I(a) or a pharmaceutically acceptable salt thereof, and, if desired, converting by methods known per se the product in the form of the free acid or silyl ester or salt thereof to the corresponding free acid or pharmaceutically acceptable salt thereof.

Acylation of a 7-amino group of a cephalosporin is a well-known reaction and any of the functional equivalents of formula III or III(a) commonly used as acylating agents for primary amino groups may be employed. Examples of suitable acylating derivatives of the free acid include the corresponding acid anhydrides, mixed anhydrides, e.g. alkoxyformic anhydrides, acid halides, acid azides, active esters and active thioesters. The free acid may be coupled with compound II after first reacting said free acid with N,N'-dimethylchloroforminium chloride or by the use of enzymes or of an N,N'-carbonyldiimidazole or an N,N'-carbonylditriazole or a carbodiimide reagent, e.g. N,N-diisopropylcarbodiimide. N,N'-dicyclohexylcarbodiimide or N-cyclohexylcarbodiimide or N-cyclohexyl-n'-(2-morphilinoethyl) carbodiimide or of an alkylylamine reagent or of an isoxasolium slt reagent. Another equivalent of the free acid is a corresponding azolide, i.e., an amide of the corresponding acid whose amide nitrogen is a member of a quasiaromatic five membered ring containing at least two nitrogen atoms, i.e. imidazole, pyrazole, the triazoles, benzimidazole, benzotriazole and their substituted derivatives. A reactive derivative of the phenylglycine acid of formula III is the N-carboxy anhydride (Leuch's anhydride). In this structure the group which activates the carboxyl group also serves to protect the amino group. A particularly preferred acylating agent is the acid chloride hydrochloride of the formula

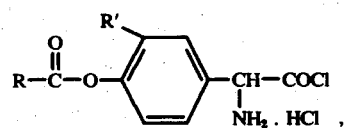

which also serves a dual function of carboxyl activation and amino protection. Mention was made above of the use of enzymes to couple the free acid with its blocked amino group with compound II. Included in the scope of such processes are the use of an ester, e.g. the methyl ester, of that free acid with enzymes provided by various microorganisms, e.g. those described by T. Takahashi et al., *J. Amer. Chem. Soc.*, 94(11), 4035–4037 (1972) and by T. Nara et al., *J. Antibiotics* (Japan), 24(5), 321–323 (1971) and in West Germany No. 2,216,113.

The particular process conditions, e.g. temperature, solvent, reaction time, etc. selected for the coupling reaction are determined by the nature of the acylation method used and are known to those skilled in the art. Generally it is useful to add an organic tertiary amine, e.g. triethylamine, N,N-dimethylaniline, ethylpiperidine, 2,6-lutidine or quinoline, to serve as a proton acceptor or salt-forming agent.

The compounds of the present invention may be isolated in any of the ways customarily employed for the isolation of similar cephalosporins. Thus, the product may be obtained as the neutral molecule and, in the case of compounds of formula I, this is probably more accurately represented as the zwitterion, or it may be isolated as a salt. Formation of the desired pharmaceutically acceptable carboxylic acid or acid addition salt is carried out by known methods, e.g. reaction of the acid with an appropriate base or acid.

At the conclusion of the acylation reaction the product obtained may be converted (before or after removal of the amino-protecting group) by methods known per se to another desired product of formula I. For example, the product of formula I or I(a) in the form of a silyl ester or salt thereof may be converted to the free acid product or pharmaceutically acceptable salt thereof by removal of the silyl ester group, e.g. by hydrolysis.

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle. The peferred compounds have also been unexpectedly found to be efficiently absorbed upon oral administration.

The novel medicaments provided by the present invention may be formulated as pharmaceutical compositions comprising, in addition to the active ingredient, a pharmaceutically acceptable carrier of diluent. The compounds may be administered both orally and parenterally. The pahmaceutical preparations may be in solid form such as capsules, tablets or emulsions. In the treatment of bacterial infections in man, the compounds of this invention may be administered parenterally in an amount of from about 5 to 200 mg./kg./day in divided dosage, e.g. 3 to 4 times a day. They are administered in dosage units containing e.g. 125, 250 or 500 mg. of active ingredients with suitable physiologically acceptable carriers or excipients.

The following illustrates the preparation of starting materials used in the production of the novel compounds of the invention.

Starting Materials

Synthesis of potassium 1,2,3-triazole-5-thiolate

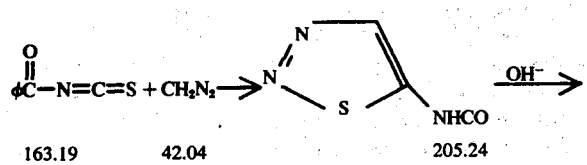

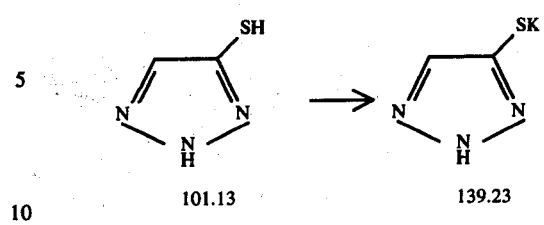

The synthesis of the thiol was accomplished by a procedure essentially identical to that described in the literature [J.Goerdler and G. Gnad, Chem. Ber. 99, 1618 (1966)].

5-Benzamido-1,2,3-thiadiazole

To a stirred solution of benzoylisothiocyanate (50.6 g., 310 mmoles) in commercial anhydrous ether (400 ml.), maintained at 0° and in a nitrogen atmosphere, was added dropwise with vigorous stirring, 0.685 N ethereal diazomethane (453 ml., 310 mmoles). When the addition was completed, the mixture was stirred for 1 hour at 0°, the solid was collected by filtration and dried in vacuo. The melting point of the crude material (23.3 g.) thus obtained was observed somewhere in the region 232° to 257°. Goerdler reported m.p. 267° for the pure material. A small second crop (2.1 g.) was obtained by evaporation of the mother liquor in vacuo. The total yield was therefore 40%.

1,2,3-Triazole-5-thiol

A solution of the above benzamido compound (8.2 g., 40 mmoles) in 2N sodium hydroxide (80 ml., 160 mmoles) was heated under reflux temperature in a nitrogen atmosphere for 24 hours. The solution was cooled to 0° in ice, and concentrated hydrochloric acid (26 ml.) was added, while a continuous stream of nitrogen was passed through the solution. The benzoic acid which precipitated was collected by filtration; the filtrate was saturated with sodium chloride and the additional benzoic acid which separated was removed by filtration. The filtrate was immediately extracted with ethyl acetate, the extract was washed with saturated salt solution, dried over magnesium sulfate and then evaporated in vacuo. The viscous oil which remained was immediately evaporated distilled in vacuo (70–75°10.001 mm.) to give an oil (2.84 g., 70%) which solidified (m.p. 52°–59°; Goerdler reported m.p. 60°) spontaneously.

Potassium 1,2,3-Triazole-5-thiolate

To a solution of the above thiol (2,84 g., 28.1 mmoles) in absolute ethanol (28 ml.) was added 1.93 N alcoholic potassium hydroxide solution (14.5 ml.). The solution was then diluted with anhydrous ether until crystallization of the salt was completed. The solid was collected by filtration, washed with ether, and dried in vacuo. The salt obtained in this manner (3.65 g., 93%) had m.p. 225° with decomposition.

It is important to note that the conversion of the benzamido thiadiazole to the triazole thiol is known to proceed via 5-amino-1,2,3-thiadiazole [G. Goerdler and G. Gnad, Chem. Ber. 99, 1618 (1966)].

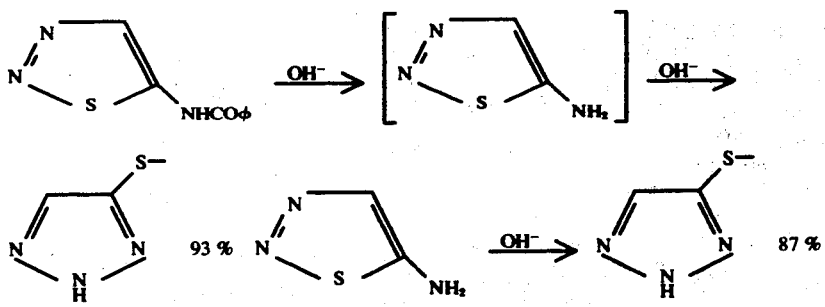

5-Amino-1,2,3-thiadiazole can be prepared by an alternative route, not involving diazomethane [D. L. Pain and R. Slack, J. Chem. Soc. 5166 (1965)].

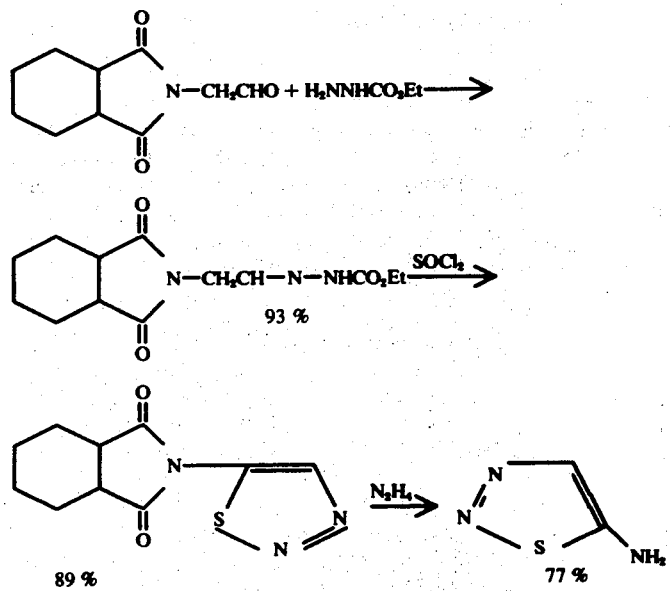

Synthesis of 7-Amino-3-(1,2,3-triazol-5-ylthiomethyl)-3-cephem-4-carboxylic acid The reactions were conducted under a nitrogen atmosphere in a reaction vessel protected from light. The water and phosphate buffer were gassed vigorously with nitrogen prior to use to displace oxygen.

5-Amino-1,2,3-thiadiazole (10.3 g., 0.102 mole) was added to a solution of 8.16 g. of sodium hydroxide in 100 ml. of water. The mixture was heated rapidly to reflux and then refluxed for 10 min. to rearrange 5-amino-1,2,3-thiadiazole to 5-mercapto-1,2,3-triazole. To the reaction mixture containing 5-mercapto-1,2,3-triazole cooled in an ice bath was added 1100 ml. of ice cold 0.1M pH 6.4 phosphate buffer. The solution, which was at pH 10.5, was adjusted to pH 8.5 with 42% phosphoric acid. 7-Aminocephalosporanic acid (21.8 g., 0.08 mole) was added and the mixture heated at 50° for 4 hours. The clear solution was cooled in an ice bath and adjusted to pH 4.5 with conc. HCl. The precipitated product was collected by filtration, washed with water and air dried; 16.2 g.

The crude product (15.2 g.) was brought into solution with 600 ml. of methanol and 40 ml. of conc. HCl. After carbon treatment the solution was diluted with 1.5 l. of ice water and extracted once with ethyl acetate. The aqueous phase was concentrated at reduced pressure to remove methanol. The cold aqueous concentrate was adjusted slowly to pH 4.0 with 20% sodium hydroxide causing crystallization of the product. The product was collected by filtration, washed with water and methanol and dried in vacuo over phosphorus pentoxide; 11.4 g. The IR and NMR spectra were fully consistent for the desired product.

Anal. Calcd. for $C_{10}H_{11}N_5O_3S_2$: C, 38.42; H, 3.55; N, 22.40. Found: C, 38.27, 38.26; H, 3.76, 3.40; N, 21.02, 21.00; $H_2O$, 1.70.

Purification of 7-Amino-3-(1,2,3-triazol-5-ylthiomethyl)-3-cephem-4-carboxylic acid (II)

Crude 7-amino-3-(1,2,3-triazol-5-ylthiomethyl)-3-cephem-4carboxylic acid (16.1 g.) containing approximately 20 mole % of 7-aminocephalosporanic acid as an impurity, was brought into solution with 600 ml. of methanol and 40 ml. of conc. HCl. After carbon treatment, the solution was diluted with 1.5 l. of ice water and extracted once with ethyl acetate. The aqueous phase was concentrated at reduced pressure to remove methanol. The cold aqueous concentrate was then adjusted slowly to pH 4.0 with 20% sodium hydroxide causing the product to crystallize. The product was collected by filtration, washed with water and methanol and dried in vacuo over phosphorus pentoxide; 11.4 g.

The NMR spectrum indicated that this product contained about 7 mole % of 7-aminocephalosporanic acid as an impurity.

The above purification procedure was repeated on 11.4 g. of the product using 425 ml. of methanol, 28 ml. of conc. HCl and 1 l. of ice water yielding 8.0 g. of product. The NMR spectrum was fully consistent for the desired product and indicated no trace of 7-aminocephalosporanic acid as an impurity.

Anal. Calcd. for $C_{10}H_{15}N_5O_3S_2$: C, 38.42; H, 3.55; N, 22.40. Found: C, 39.06, 38.53; H, 3.56, 3.51; N, 22.05, 21.60; $H_2O$, 1.78.

7-Amino-3-(1,2,3-triazole-5-ylthiomethyl)-3-cephem-4-carboxylic acid (II)

Ten grams (0.075 mole) of 5-mercapto-1,2,3-triazole potassium salt was added to a stirred slurry of 19 g. (0.07 mole) of purified 7-aminocephalosporanic acid and 5.9 g. (0.07 mole) of $NaHCO_3$ in 350 ml. of 0.1 M phosphate buffer (pH 6.4) and the mixture heated and stirred at 55° C. for 3½ hours under a nitrogen atmosphere. The resulting solution was cooled to 22° C. and adjusted to pH 5.5 with 40% $H_3PO_4$. The resulting precipitate was filtered off, washed with cold water (50 ml.) and air dried. The yield of 7-amino-3-(1,2,3-triazole-5-ylthiomethyl)-3-cephem-4-carboxylic acid was 8 g., dec. pt. 230° C. IR analysis showed some decomposition of the β-lactam ring but it was used "as is" for the next step.

Anal. Calcd. for $C_{10}H_{11}N_5O_3S_2$: C, 38.39; H, 3.54. Found: C, 38.36; H, 3.78.

7-Amino-3-(1,2,3-triazol-5-ylthiomethyl)-3-cephem-4-carboxylic acid (II)

Two hundred seventy-two g. (1.0 mole) of 7-aminocephalosporanic acid was suspended in 3000 ml. of 0.1M phosphate buffer, pH 6.4, and 150 ml. of methyl isobutyl ketone followed by 84 g. (1.0 mole) of sodium bicarbonate (Note: The sodium bicarbonate was added in portions). Then 143 g. (1.0 mole) of 5-mercapto-1(H)-1,2,3-triazole potassium salt was added and the mixture stirred at 55° C. ± 1° C. under a nitrogen atmosphere for 4 hours. After 1 hr. the pH was readjusted to 6.4 by addition of a small amount of 40% $H_3PO_4$. At the end of the 4 hr. heating period, 50 g. of "Darco KB" decolorizing charcoal was added and, after stirred for 15 min. at 55° C., the slurry was filtered hot through a diatomaceous earth ("Celite") pad. The pad was washed with 3 × 100 ml. water. The pH of the combined filtrates was adjusted while hot to 4.5 by slow addition of 6 N HCl. After cooling 30 min. at 0° C., the crude product was collected by filtration, washed with 2 × 200 ml. of cold water followed by 2 × 1000 ml. of methanol and air dried.

The crude product was suspended in 3000 ml. of 50% methanol-water and 300 g. (1.5 mole) of p-toluenesulfonic acid was added. The mixture was stirred for 15 min. and then 50 g. of "Darco KB" decolorizing charcoal was added. After stirring for 15 min. at 22° C., the slurry was filtered through a "Celite" pad and the pad washed with 2 × 100 ml. of 50% methanol-water. The pH of the combined filtrates was adjusted to 4.0 by addition of approximately 210 ml. of triethylamine. After cooling at 0° C. for 1 hour the product was collected by filtration, washed with 2 × 400 ml. of 50% methanol-water and then 2–1000 ml. of methanol and air dried.

This material was suspended in 2000 ml. of water and 84 g. (1 mole) of sodium bicarbonate was added. After stirring for 10 min. at 22° C., 50 g. of "Darco KB" charcoal was added and, after stirring for 15 min. at 22° C. the slurry was filtered through a "Celite" pad. The product was washed with 2 × 100 ml. of water and the pH of the combined filtrates was adjusted to 3.5 by slow addition of 6 N HCL. After stirring for 10 min. at 22° C., the mixture was cooled to 0° C. for 1 hr. The product was collected by filtration was washed with 2 × 200 ml. of cold water and 2 × 1000 ml. of acetone. After drying over $P_2O_5$ in a vacuum desiccator for 14 hr. at room temperature the yield was 100 g.; dec. pt. 230° C. The IR and NMR were consistent for the desired structure.

Preparation of D
(-)2-amino-2-(4-acetoxyphenyl)acetic acid

Method A (in acetic acid as solvent)

203.5 g (1 Mole) of D(—)p-hydroxyphenylglycine chloride 800 ml of acetic acid and 314 g (4 Moles) of acetyl chloride are stirred 48 hours at room temperature. The solid is collected, washed three times with acetone (3 × 250 ml) and twice with ethanol (2 × 250 ml) and dried at 40°. Yield 210 g (85.4%). This hydrochloride is dissolved in 3.0 l of water; the solution is cooled to +5 to 10° C and the pH adjusted to 4.5 with 20% $NH_4OH$. The suspension is stirred 1 hour at 5° C and the solid collected, washed twice with water and twice with acetone, and dried at 40° C. Yield 133 g (64% from D(—)p-hydroxy phenyl glycine). αD (1% HCl N/10) = —104.5

Method B (in methylene chloride)

4.07 g (0.02 Mole) of D(—)p-hydroxyphenylglycine hydrochloride 30 ml of methylene chloride and 6.28 g (0.08 Mole) of acetyl chloride are stirred 48 hours at room temperature. The solid is collected, washed twice with acetone and twice with ethanol.

Yield 4.17 g (84.5%). Anal. cl = 14.8% (calculated 14.4%)

Method C (in trifluoroacetic acid)

1.67 g (0.01 Mole) of D(—)p-hydroxyphenylglycine is added with stirring, to 10 ml of trifluoroacetic acid at room temperature. After dissolution, 1.57 g (0.02 Mole) of acetyl chloride is added. After a slightly exothermic reaction, a solid appears. The suspension is stirred 1½ hours at room temperature and the trifluoroacetic acid is removed in vacuum. The remaining solid is collected, washed with methylene chloride and with ethanol. The D(—)2-amino-2-(4-acetoxyphenyl)acetic acid is identical to that prepared by methods A or B.

Yield: 1.9 g (75%)

Preparation of D
(-)2-amino-2-(4-pivalyloxyphenyl)acetic acid hydrochloride 1.67 g (0.01 Mole) of D(-)p-hydroxyphenylglycine is added to 10 ml of trifluoroacetic acid, followed by 2.4 g (0.02 Mole) of pivalyl chloride. The resulting solution is stirred 24 hours at room temperature and vacuum concentrated to dryness. The solid is collected and washed with ether.

Yield: 2.56g (89%).

This hydrochloride is recrystallized from isopropanol.

Anal. Cl = 11.8% (calculated 12,3%) UV λmax. 205 nm and 220 nm

Preparation of D (-)2 amino-2-(4-Benzoyloxyphenyl)acetic acid hydrochloride

This compound is prepared according to the same procedure as used for the pivalyloxy derivative. Yield: 2.7 g (87%). An analytical sample is recrystallized from ethanol.

Anal. cl = 11.3% (calculated 11.5%) UV λ max. 205 nm and 234 nm

Preparation of D (—)2-amino-2-(4-acetoxyphenyl)acetyl chloride hydrochloride 83.6 g. (0.40 mole) of D(—)2-amino-2-(4-acetoxyphenyl)-acetic acid and 1.25 l. of anhydrous methylene chloride are cooled to −5° C. with stirring. Then 152 g. of phosphorous pentachloride are slowly added followed by 4 ml. of dimethyl formamide. The mixture is stirred 4 hours at 0° C. The solid is collected, washed with anhydrous methylene chloride and vacuum dried at room temperature.

Yield: 61 g. (57.5%). Anal. Total chlorine = 27.2% (Theory 26.9%)

Preparation of D-(—)2-formyloxy-2-(4-formyloxyphenyl)acetic acid

A solution of 3.6 g. (0.02 mole) of D-(—)-2-hydroxy-2-(4-hydroxyphenyl) acetic acid in 50 ml. of 97% aqueous formic acid was allowed to react at 22° C. for approximately 68 hours. The excess formic acid was removed by distillation at 22° C. under reduced pressure. The residue is extracted with diethyl ether; the ethereal layer is dried over sodium sulfate, filtered and evaporated to afford the desired product.

Preparation of D-(—)2-formyloxy-2-(4-acetoxyphenyl)acetic acid

The D-(—)2-formyloxy-2-(4-formyloxyphenyl)acetic acid obtained above is dissolved in 10 ml. of acetyl chloride and the resulting mixture was allowed to stand at 22° C. for 20 hours. The excess acetyl chloride was distilled off under reducing pressure; the residue was treated with benzene and the benzene then removed under vacuum to afford the desired product which analyzed as 60% pure according to NMR.

DESCRIPTION OF THE PREFERRED EMBODIMENTS

The following examples are given in illustration of, but not in limitation of, the present invention. All temperatures are in degrees Centigrade. 7-Aminocephalosporanic acid is abbreviated as 7-ACA and 7-aminodesacetoxycephalosporanic acid as 7-ADCA.

EXAMPLE 1

7-D(—)2-amino-2-(4-acetoxyphenylacetamido)-desacetoxycephalosporanic acid — (acetoxy cephalexine) — RN 1394

15.27 g (0.0714 Mole) of 7-ADCA are stirred in 500 ml of anhydrous methylene chloride; 120 ml of methylene chloride are distilled off and 11.8 ml of hexamethyldisilazane are added. The mixture is stirred and refluxed 20 hours (after about 10–15 hours all the 7-ADCA is run in solution). The above solution is cooled to 0° C and 120 ml of methylene chloride followed by the addition of 9.5 ml of dimethylaniline and 7 ml of a solution of dimethylaniline hydrochloride in methylene chloride (30%). Then 20 g (0.0756 Mole) of D(—)2-amino-2-(4-acetoxyphenyl)acetyl chloride, hydrochloride are added in small portions (≃ 1½ hours) at 0° C. The mixture is stirred 30 min. at +10° C and 4 hours at +20° C and allowed to stand overnight at +5° C. Then 5 ml of methanol followed by 240 ml of water are added. The pH is adjusted at 2.5 with triethylamine and the mixture is filtered through a celite pad; then the pH is checked and the aqueous phase is separated, washed twice (2 × 150 ml) with methylene chloride and treated with charcoal. The solution is adjusted to pH 4.5 and vacuum concentrated to a volume of ≃ 150 ml. The suspension is allowed to stand overnight at +5° C and the solid collected and washed with water and acetone, and dried at 40° C.

Yield: 15.1 g (≃ 50% of 75–80% pure material) (αD (1% H$_2$O) = +107

14 g of this crude material is suspended in 30 ml of water (pH = 3.2); hydrochloric acid (36%) is added to pH 1.3 and the resulting solution is charcoal treated and filtered through a celite pad and adjusted to pH 4–4,5 over stirring. After 2 hours at 0°–+5° C the RN 1394 is collected, washed with water and acetone and dried at 40° C.

Yield: 7 g. αD(1% H$_2$O) = +133.

The infrared and nuclear magnetic resonance spectra are consistent with the desired product.

Biological Data

Table I shows comparative MIC data for BL-S 578-4 (p-hydroxy analogue of cephalexin) and (p-acetoxycephalexin (RN 1394). Minimal inhibitory concentrations were determined by the 2-fold broth dilution method utilizing equimolar concentrations of each compound.

Table I

| Nutrient Broth Organisms | | MIC (μg/ml) BL-S 578-4 p-hydroxy-cephalexin | p-acetoxy-cephalexin RN 1394 |
|---|---|---|---|
| D. pneumoniae* (10-3)** | A9585 | 0.6 | .08 |
| Str. pyogenes* (10-3)** | A9604 | .08 | .08 |
| S. aureus Smith (10-4) | A9537 | 1.3 | 0.6 |
| S. aureus + 50% serum (10-4) | A9537 | 1.3 | 0.6 |
| S. aureus BX1633 (10-3) | A9606 | 2 | 1 |
| S. aureus BX1633 (10-2) | A9606 | 2 | 2 |
| S. aureus Meth-Res (10-3) | A15097 | 16 | 32 |
| Sal. enteritidis (10-4) | A9531 | 8 | 8 |
| E. coli Juhl (10-4) | A15119 | 16 | 32 |
| E. coli (10-4) | A9675 | 32 | 63 |
| K. pneumoniae (10-4) | A9977 | 16 | 16 |
| K. pneumoniae (10-4) | A15130 | 32 | 32 |
| Pr. mirabilis (10-4) | A9900 | 8 | 8 |
| Pr. morganii (10-4) | A15153 | >125 | >125 |
| Ps. aeruginosa (10-4) | A9843A | >125 | >125 |
| Ser. marcescens (10-4) | A20019 | >125 | >125 |
| Ent. cloacae (10-4) | A9656 | >125 | >125 |
| Ent. cloacae (10-4) | A9657 | 16 | 8 |

EXAMPLE 2

7-[D(−)2-amino-2-(4-acetoxyphenylacetamido]-3-[(1,2,3,-Triazol-5-yl)-thiomethyl]-3-cephem-4-carboxylic acid: RN 1396

62.6 g (0.2 mole) of 7-amino-3-[(1,2,3-Triazol-5-yl)thiomethyl]-3-cephem-4-carboxylic acid (7-TACA), 1.5 l of methylene chloride and 60.2 g (0.374 mole) of hexamethyl disilazane are stirred and refluxed 20 hours with a slight pressure of nitrogen (after about 2 hours all 7-TACA is run in solution). The solution is cooled to 0° C and 30.4 ml of dimethylaniline, followed by 20.4 ml of a solution of dimethylaniline hydrochloride in methylene chloride (30%) and 1.35 g of imidazole are added.

Then 60.5 g (0.229 mole) of 2-amino-2-(4-acetoxyphenyl)acetyl chloride hydrochloride are added in small portions ( ≃ 1½ hour) at 0° C. The mixture is then stirred 3 hours at 20° C and let stand overnight at +5° C. 25 ml of methanol followed by 750 ml of water are then added. The pH is adjusted to 2.3–2.5 with triethylamine and the mixture is filtered through a celite pad. The aqueous phase is separated, washed twice with methylene chloride and charcoal treated. The solution is adjusted to pH 4.3 and stirred 2 hours at +5° C. The solid is collected, washed twice with water and dried at 40° C. Yield: 53 g (about 50%). This crude material is purified twice as follows: The solid is treated with eight volumes of 0.5 N hydrochloric acid and the suspension is decolorized with charcoal. An equal volume of methanol is added to the solution and the pH adjusted to 2–2,1; after 15 minutes a small amount of suspended solid is collected and discarded. The filtrate is adjusted to pH 4. The precipitated solid is collected, washed with MeOH/H$_2$O (50/50) and pure methanol.

Yield: 25 g. (after two purifications).
— IR consistent with assigned structure
— Moisture (KF) : 5.1%
— Chemical assay
— Iodometric assay 885 mcg/mg
— Potentiometry Amine assay: 97%

Biological Data

Table II shows comparative MIC data for the above prepared 7-[D(2-amino-2-(4-acetoxyphenylacetamido)]-3-[1,2,3-triazole-5-yl)-thiomethyl]-3-cephem-4-carboxylic acid, RN-1396, and its p-hydroxy analogue, BL-S640. Minimal inhibitory concentrations were determined by the 2-fold broth dilution method utilizing equimolar concentrations of each compound.

Table II

| Nutrient Broth Organisms | | MIC (μg/ml) | |
|---|---|---|---|
| | | Bl-S640 | p-acetoxy BL-S640 hydrate RN 1396 |
| D. pneumoniae* (10-3)** | A9585 | .04 | .04 |
| Str. pyogenes* (10-3)** | A9604 | .04 | .04 |
| S. aureus Smith (10-4) | A9537 | 0.3 | 0.16 |
| S. aureus + 50% serum (10-4) | A9537 | 1 | 1 |
| S. aureus BX1633 (10-3) | A9606 | 0.6 | 0.6 |
| S. aureus BX1633 (10-2) | A9606 | 1 | 4 |
| S. aureus Meth-Res (10-3) | A15097 | 4 | 8 |
| Sal. enteritidis (10-4) | A9531 | 0.6 | 0.3 |
| E. coli Juhl (10-4) | A15119 | 0.5 | 2 |
| E. coli (10-4) | A9675 | 4 | 8 |
| K. pneumoniae (10-4) | A9977 | 0.5 | 1 |
| K. pneumoniae (10-4) | A15130 | 1 | 2 |
| Pr. mirabilis (10-4) | A9900 | 0.5 | 0.5 |
| Pr. morganii (10-4) | A15153 | 63 | 63 |
| Ps. aeruginosa (10-4) | A9843A | 125 | 125 |
| Ser. marcescens (10-4) | A20019 | 125 | 125 |
| Ent. cloacae (10-4) | A9656 | 125 | 125 |
| Ent. cloacae (10-4) | A9657 | 0.5 | 1 |
| Ent. cloacae (10-4) | A9659 | 32 | 32 |

*45% AAB + 5% serum + 50% NB
**Dilution of overnite broth culture

EXAMPLE 3

7-D-(−2-(4-acetoxyphenyl)-2-formyloxyacetamido]-3-(1-methyl-1,2,3,4-tetrazol-5-yl)thiomethyl-3-cephem-4-carboxylic acid To a solution of 4.8 g. (0.02 mole) of crude D-(−)2-formyloxy-2-(4-acetoxyphenyl)acetic acid and 25 ml. of diethyl ether was added one drop of dimethylformamide and 5 ml. of oxalyl chloride. After stirring at 22° C. for 1 hour, the solvent was removed and the residue dissolved in 25 ml. of acetone, the resulting solution was added dropwise to a solution of 6.3 g. (0.02 mole) of 7-amino-3-(1-methyl-1,2,3,4-tetrazol-5-yl) thiomethyl-3-cephem-4-carboxylic acid, 5.6 g. of sodium bicarbonate, 300 ml. of water and 80 ml. of acetone at approximately 3° C. The reaction mixture was stirred for 1 hour at 3° to 5° C. followed by removal of the acetone. The pH of the residue was adjusted to 2.0 by the addition of 40% aqueous phosphoric acid under a layer of ethyl acetate. The aqueous layer was extracted with 2 × 100 ml. of ethyl acetate and the combined organic layers dried over sodium sulfate. The organic layers were filtered and the filtrate evaporated under vacuum to an oil. Trituration of the oil with diethyl ether afforded 8 g. of solid product which analyzed by NMR to have 85–90% acetyl and 50–60% formyl.

EXAMPLE 4

7-D-(−)[2-(4-formyloxyphenyl)-2-formyloxyacetamido]-3-(1-methyl-1,2,3,4-tetrazol-5-yl)thiomethyl-3-cephem-4-carboxylic acid.

The same procedure as in Example 3 was followed to react 2.5 g. (0.01 mole) of D-(−)2-formyloxy-2-(4-formyloxyphenyl)-acetic acid with 3.28 g. (0.01 mole) of 7-amino-3-(1-methyl-1,2,3,4-tetrazol-5-yl) thiomethyl-3-cephem-4-carboxylic acid to afford after trituration with diethyl ether 4.2 g. of desired product which solids had a decomposition point of 160°-5° C., an infrared and NMR spectrum consistent with its structure but containing a by-product.

Microanalysis of the desired product gave:
Calc'd. for C$_{20}$H$_{18}$N$_6$O$_8$S$_2$:

---

Table I-continued

| Nutrient Broth Organisms | MIC (μg/ml) | |
|---|---|---|
| | BL-S 578-4 p-hydroxy-cephalexin | p-acetoxy-cephalexin RN 1394 |
| Ent. cloacae (10-4) A9659 | >125 | >125 |

*45% AAB + 5% serum + 50% NB
**Dilution of overnite broth culture

|   | % Theory | % Found |
|---|---|---|
| C | 44.86 | 46.47 |
| H | 3.38 | 4.14 |
| N | 15.70 | 13.50 |
| K.F. (H$_2$O) |  | 1.78 |

In addition to the above, the compounds of the instant invention are also valuable as intermediates for the preparation of other pharmaceutically active compounds. For example, the instant α-formyloxy or α-amino-α-(p-acyloxyphenyl)acetamido cephalosporanic acids may be converted to the corresponding p-hydroxy compounds which are known to be potent antibacterial agents useful in the treatment of infectious diseases in poultry and animals, including man, caused by many Gram-positive and Gram-negative bacteria. The conversion can be carried out chemically by simple acid or base hydrolysis in an aqueous medium in most circumstances.

We have found that 7-D-(—)α-amino-α-(p-acetoxyphenyl-acetamido) desacetoxycephalosporanic acid, although stable in normal saline, is hydrolyzed enzymatically to the known and potent 7-D-(—)α-amino-α-(p-hydroxyphenylacetamido)desacetoxycephalosporanic acid.

Accordingly, the present invention also provides for a novel process for preparing 7-D-(—)α-amino-α-(p-hydroxyphenylacetamido)desacetoxycephalosporanic acid, hydrate or a pharmaceutically acceptable salt thereof, which process comprises treating in an aqueous solution 7-D-(—)α-amino-α-(p-acetoxyphenylacetamido)desacetoxycephalosporanic acid with an esterase at a pH between about 5.0 and about 7.5; isolating the product by methods known per se, and, if desired, converting by methods known per se, the product in the form of the free acid or hydrate to the corresponding pharmaceutically acceptable salt thereof.

A preferred embodiment is the preparation of 7-D-(—)-α-amino-α-(p-hydroxyphenylacetamido)-desacetoxycephalosporanic acid, hydrate or a pharmaceutically acceptable salt which process comprises treating in aqueous solution 7-D-(—)-α-amino-α-(p-acetoxyphenylacetamido)desacetoxycephalosporanic acid with an esterase selected from human serum, animal serum, citrus esterase, wheat bran, wheat germ, and bacillus subtilis at a pH between about 5.0 and about 7.5 and at a concentration of about 5 to about 10 mg./ml. of esterase per total volume of the aqueous solution; isolating the product by methods known per se, and, if desired, converting the product in the form of free acid or hydrate to the corresponding pharmaceutically acceptable salt thereof.

A commercially preferred embodiment of the present invention is the preparation of 7-D-(—)α-amino-α-(p-hydroxyphenylacetamido)desacetoxycephalosporanic acid, hydrates or pharmaceutically acceptable salts thereof, which process comprises:

treating in an aqueous solution 7-D-(—)-α-amino-α-(p-acetoxyphenylacetamido)cephalosporanic acid with an esterase selected from citrus esterase, wheat bran, and wheat germ at a pH between about 5.0 and about 7.5 and at a concentration of about 5 to about 10 mg./ml. of esterase per total volume of the aqueous solution; and isolating the product by methods known per se, and, if desired, converting the product in the form of the free acid or hydrate to the corresponding pharmaceutically acceptable salt thereof.

Of special commercial interest is the process for preparing 7-D-(—)α-amino-α-(p-hydroxyphenylacetamido)desacetoxycephalosporanic acid, hydrate or pharmaceutically acceptable salt thereof comprising:

treating in an aqueous solution 7-D-(—)-α-amino-α-(p-acetoxyphenylacetamido)desacetoxycephalosporanic acid with the commercially available esterase, coarse wheat bran, at a pH between 5.5 and 6.0 or optionally in the presence of a buffer at a pH of 7.0 at a concentration of about 10 mg./ml. of esterase per total volume of solution; and isolating the product by methods known per se, and, if desired, converting the product in the form of a free acid or hydrate to the corresponding pharmaceutically acceptable salt thereof.

The 7-D-(—)α-amino-α-(p-hydroxyphenylacetamido)desacetoxycephalosporanic acid prepared by the instant invention is known to be a potent antibacterial agent useful in the treatment of infectious diseases in poultry and animals, including man, caused by many Gram-positive and Gram-negative bacteria.

The following example illustrates the preparation of p-acetoxycephalexin according to the invention.

EXAMPLE A

Solutions of 0.5 mg./ml. of 7-D-(—)α-amino-α-p(-acetoxyphenylacetamido)desacetoxycephalosporanic acid (p-acetoxycephalexin) in normal saline and in human serum were prepared. Standard solutions of 0.5 mg./ml. of 7-D-(—)α-amino-α-p(-hydroxyphenylacetamido)desacetoxycephalosporanic acid (p-hydroxycephalexin) were also prepared in both normal saline and human serum.

All the above solutions were incubated at 37° C. with shaking and sampled for chromatography at time intervals of 0, 2, 4, 8 and 24 hours. The solutions, approximately 5 microliters per strip, were spotted on Whatman No. 1 half-inch strips which were dried and developed in a solvent system containing 80 parts butylacetate; 15 parts n-butanol; 40 parts acetic acid; and 24 parts water. The strips were then bioautographed on plates seeded with *bacillus subtilis* at a pH of 6.0.

The biochromatograms indicated that p-acetoxycephalexin is quickly hydrolyzed to the p-hydroxy form in human serum but appears stable in normal saline.

What we claim is:

1. The compound which is 7-D-α-amino-α-(p-acetoxyphenylacetamido)-3-[(1,2,3-triazol-5-yl)-thiomethyl]-3-cephem-4-carboxylic acid when substantially free of the L isomer.

* * * * *